United States Patent [19]

Donnerhack et al.

[11] Patent Number: 4,838,270
[45] Date of Patent: Jun. 13, 1989

[54] CABIN FOR CARRYING OUT CRYOTHERAPY ON THE ENTIRE BODY

[75] Inventors: Andreas Donnerhack, Krefeld; Klemens Thoma, Krefeld-Huls; Wolfgang Volker, Tonisvorst; Rolf-Dieter Gallmeister; Thomas Stratz, both of Bad Sackingen; Ludwig Lammers, Idstein, all of Fed. Rep. of Germany

[73] Assignee: Messer. Griesheim GmbH, Fed. Rep. of Germany

[21] Appl. No.: 933,015

[22] Filed: Nov. 20, 1986

[30] Foreign Application Priority Data

Nov. 22, 1985 [DE] Fed. Rep. of Germany ....... 3541332
Jul. 23, 1986 [DE] Fed. Rep. of Germany ....... 3624822

[51] Int. Cl.⁴ .................... A61H 33/06; A61H 33/00; A61F 7/00; F25D 23/12
[52] U.S. Cl. .................... 128/371; 128/367; 128/400; 128/DIG. 27; 62/259.3
[58] Field of Search ............... 128/371, 367, 400, 369, 128/362, 365, 368, DIG. 27, 65, 66; 4/549, 535; 604/291; 312/236; 62/440, 259.3, 443

[56] References Cited

U.S. PATENT DOCUMENTS

| 311,764 | 2/1885 | Johnson | 128/400 |
| 352,386 | 11/1886 | Bailey | 128/371 |
| 3,874,374 | 4/1975 | Jacuzzi | 128/66 |
| 3,885,571 | 5/1975 | Sachs | 128/400 |
| 3,890,965 | 6/1975 | Drew | 128/66 |
| 3,918,458 | 11/1975 | Nethery | 128/400 |
| 4,161,172 | 7/1979 | Pickering | 128/400 |
| 4,170,998 | 10/1979 | Sauder | 128/400 |
| 4,525,881 | 7/1985 | Higginbotham | 128/66 |

FOREIGN PATENT DOCUMENTS 3305434 8/1984 Fed. Rep. of Germany ...... 128/400
168125 12/1981 Japan.

Primary Examiner—Richard C. Pinkham
Assistant Examiner—Mark S. Graham
Attorney, Agent, or Firm—Connolly & Hutz

[57] ABSTRACT

A device for carrying out cryotherapy on the entire body includes a treatment chamber designed as a half shell in the rear part of which are openings for the exhaust of the treatment gas and in the side parts of which are openings for the supply of the treatment gas. The openings are located in nozzle strips which may be adjusted vertically and horizontally to adjust the pattern of gas flow within the treatment chamber.

12 Claims, 1 Drawing Sheet

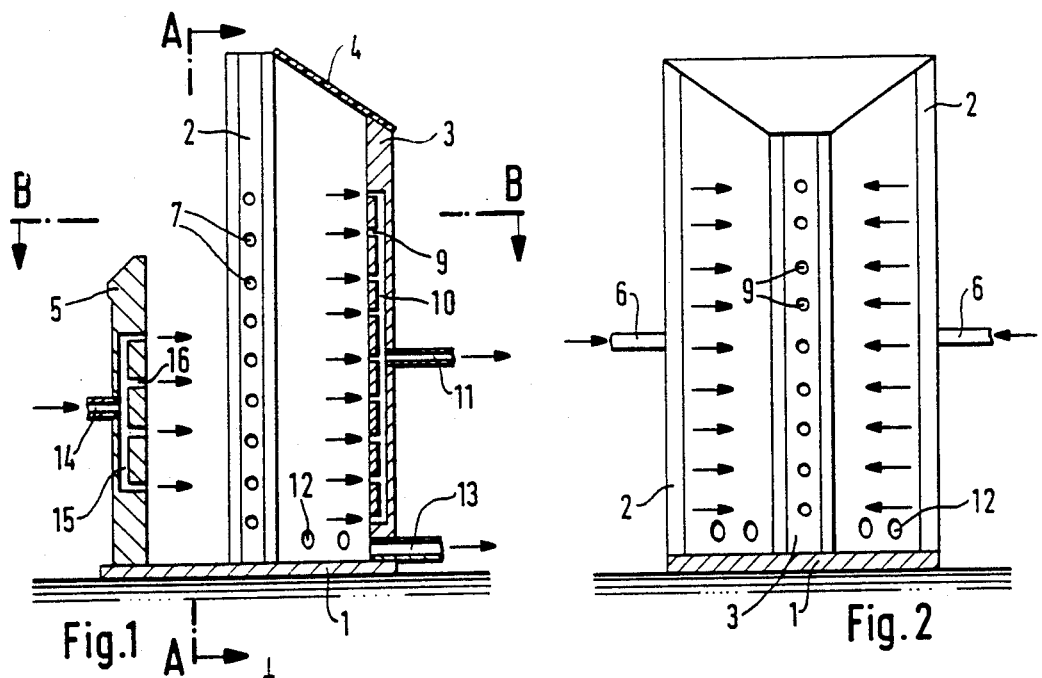
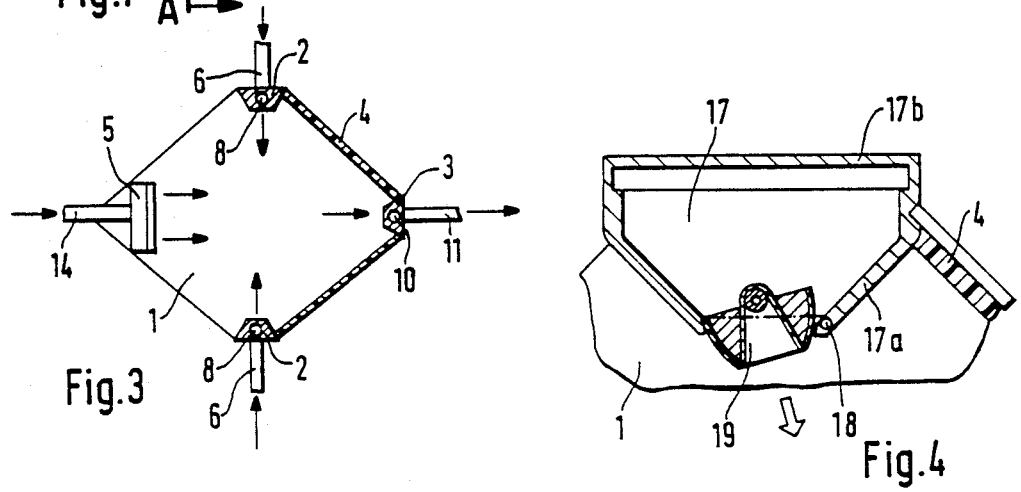
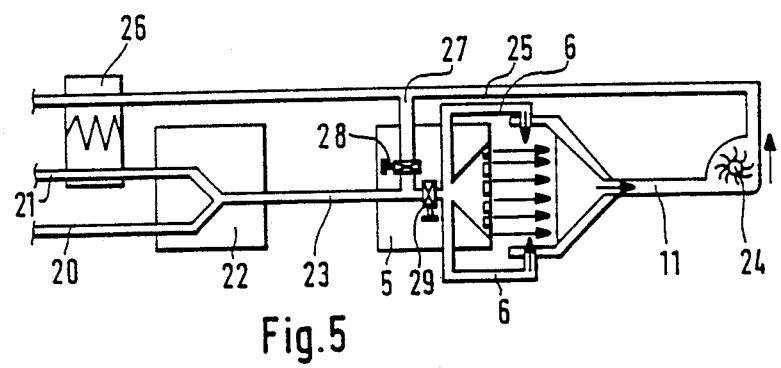

CABIN FOR CARRYING OUT CRYOTHERAPY ON THE ENTIRE BODY

BACKGROUND OF THE INVENTION

Aside from the local cryotherapy carried out since a few years ago with a cold treatment gas, e.g. for treatment of rheumatic diseases, a cryotherapy on the entire body is also carried out with some forms of illnesses. Air is hereby cooled in heat exchangers, with the aid of liquid nitrogen, and injected into closed treatment space. This treatment space which is designed as a chamber or cabin has walls of insulating material and connections for the supply and removal of the treatment gas. Such a chamber is, for example, disclosed in the Japanese utility patent No. 168 125/81. This concept finds little approval, however, from doctors as well as from patients. The reasons for this are manyfold. The patients object to the lack of direct contact with the doctor since during, treatment, only an indirect contact thru speaker arrangements is possible. The strong buildup of fog in the chamber further intensifies this impression of lack of direct contact. Another disadvantage is the cooling in the area of the patients head. Aside from this one must, by special means, avoid the inhalation of cold air. Such chambers require a high investment cost. Because of the long buildup time, there is a need for continuous operation, as a result of which relatively high operation costs result. The supervision of the patient during treatment is expensive.

SUMMARY OF INVENTION

The objective of the invention is to provide a cabin for carrying out cryotherapy on the entire body with a cold treatment gas, which permits direct contact between physician and patient during treatment, which leaves the head of the patient free, which allows the patient to leave the device at any time and which, because of shorter buildup times, does not require continuous operation.

In accordance with this invention the treatment chamber is in the form of a half shell. The rear part of the half shell has openings for the exhaust of the treatment gas and the side parts have openings for the supply of the treatment gas.

As a result of the combination of the control panel and the half shell, a treatment space, on the one hand, is obtained in which the body of the patient can be effectively impacted with cold treatment gas. On the other hand, not only is a visual and voice contact between physician and patient possible during treatment, but the physician can reach in directly, for example, in order to position the patient. In spite of this the patient can immediately leave the device at any time if he so desires for whatever reason. The supply of treatment gas can, in particular, be waived if the pressure of the treatment gas exiting from the openings in the side portions of the half shell is great enough in order to effectively impact the treatment space formed by the half shell. There is a purpose here in arranging the openings for the supply of treatment gas in vertical nozzle strips which can be shifted onto one another in the opening surface of the half shell and are rotatable about their vertical axis. This permits an individual adjustment depending upon the height and body shape of the patient. In general, at least the top outlet openings are designed so as to be adjustable so that, in the case of small patients, the head region is not impacted with the treatment gas.

THE DRAWINGS

FIG. 1 is a longitudinal section of a device for carrying out cryotherapy in accordance with this invention;

FIG. 2 is a cross-section view taken along the line A—A in FIG. 1;

FIG. 3 is a cross section view of the device along line B—B in FIG. 1;

FIG. 4 is the section through a hollow profile with tiling openings; and

FIG. 5 is an apparatus for producing the treatment gas which permits an economical idle operation of the device.

DETAILED DESCRIPTION

The device depicted in FIGS. 1 to 3 is mounted onto a foundation plate 1. The actual treatment space is formed by a half shell which essentially is formed by two lateral profiles 2 and a rear profile 3. Between the profiles 2, 3, walls 4, which consist of insulating material, are attached. At a certain distance from the openings of the half shell, a control panel is set up. The distance determined so that an optimal flow of the treatment gas before and in the half shell is set. The direction of flow is indicated by the arrows.

The supply of cold treatment gas occurs by means of the connections 6 in the lateral profiles 2. It is hereby distributed by means of a manifold 8 to the individual openings 7 through which it enters into the half shell. The treatment gas is removed from the half shell by means of appropriate openings in the rear profile 3, a manifold 10 and a connection 11.

The profiles 2, 3 are purposely hollow profiles which can be filled with foam after the placement of the manifolds 8, 10. Aside from this, additional openings 12 for the removal of the treatment gas are provided in the walls 4 in the vicinity of the foundation plate 1. These openings 12 are connected to one another by means of a manifold which discharges into the connection 13.

An additional supply of cold treatment gas occurs by means of the control panel 5 in which an appropriate connection 14 is provided. At the connection 14, a manifold 15 is connected through which the cold treatment gas arrives at the openings 16 from which it exits in the direction of the half shell. The patient enters and leaves the device via the passage formed between the control panel 5 and the half shell. Even during treatment, he can leave the device at any time if he so desires. The physician can also touch the patient during the course of the treatment and, for example, reposition him.

It is advantageous if the openings 7, 9, 12 and 16 can be individually adjusted in order to obtain specific flow patterns in the half shell. It is also of advantage if especially the openings 7 in the lateral profiles 2 can be angled so the inflowing cold treatment gas can be applied in various directions. It is also advantageous to install the openings 7 and 9 in nozzle strips which can be mounted at different heights in the profiles 2 and 3 so that openings may be laterally opposed for a horizontal gas flow. Such an embodiment is shown in FIG. 4.

The section of the hollow profile 17 illustrated in FIG. 4 corresponds to profile 2 in FIGS. 1 to 3. The hollow profile 17 composed of the upper part 17a and the lower part 17b. A nozzle strip 18 is installed in the upper part 17a. The nozzle strip 18 can, depending upon requirements, be placed at different heights in the hollow profile 17. In the nozzle strip 18, there are a number of nozzles 19 which can be angled in all directions, which corresponds to the openings 7 in FIG. 1. The nozzles 19 can also be closed individually. Such nozzles 19 are known in and of themselves from aeration technology. The control panel 5 allows the therapist to set and monitor the most important parameters.

The capability of closing individual openings 7 or nozzles 19 is important in order to adapt the device to patients of different body sizes or in order to treat specific parts of the body. As a result of the planned suctioning of the treatment gas, above all in the vicinity of the floor, the formation of a heavy mist is avoided. The ability of the patient to leave the device without being hindered by a door or a lock gives the patient the feeling that he is not at the mercy of the treatment. The acceptance of the therapy by the patient is therewith improved.

For the formation of the cold treatment gas, all commonly used devices and assemblies can be used. The treatment gas is preferably formed by mixing dry air with a cold liquified gas, preferably nitrogen. Likewise, the cold treatment gas can be produced in a heat exchanger with a cold liquified gas, preferably nitrogen.

A device suite for this purpose is illustrated in Fig. 5. Liquid nitrogen is fed into the mixing device 22 via line 20 and dry air is fed into the mixing device 22 via line 21. The cold treatment gas formed in the mixing device 22 flows through the line 23 into the control panel 5 and the connection 6 and into the treatment chamber, according to its invention which is designed as a half shell. The direction of the gas flow is indicated by non-referenced arrows. The treatment gas is channeled thru the heat exchanger 26 by means of a suction blower 24 via the line 25. The heat exchanger 26 gives up its coldness to the incoming air in line 21. In this manner, the coldness is used to optimal advantage during the operation of the device according to the invention. The exhaust causes a directed flow and serves to reclaim the coldness.

When no patient is being treated but the device needs to be left ready, the installation is switched to idle operation. During idling operation, the cold treatment gas flows directly back into the heat exchanger 26 via the line 27. The switching over to idle operation occurs by actuating the valves 28 and 29. The idle operation is purposely maintained with a small amount of gas. It only needs to assure the low temperature condition of the cold wind producing installation. The device according to the invention is thus ready even during pauses between treatments and remains ready to be first into action on short notice. Aside from the energy saving, such a manner of operation also has the advantage that the patient does not need to be positioned under cold conditions.

The device is equipped with the customary safety features which are not illustrated. It is a question, essentially, of an oxygen sensor in the region of the patient's head which triggers off a shutdown of the cooling operation in the case of a lack of oxygen. Additionally, infra-red probes can be provided which permit a consistent monitoring of the temperature on the skin surface of the patient.

SUMMARY

Cryotherapy on the entire body with cold treatment gas in closed chambers has several disadvantages. These consist of, on the one hand, psychological barriers on the patient's part since, in spite of various communication media, direct contact between the physician and the patient is not possible. On the other hand, the unwanted cooling of the patient's head occurs and precautions must be taken to prevent the patient from inhaling the cold treatment gas. In order to avoid this deficiency, the treatment chamber is designed as an open half shell. The supply of the treatment gas occurs by means of openings 9 in the rear part of the half shell. The openings for the supply of the treatment gas can be designed as vertical nozzle strips mounted at the edges of the half shell. In front of the half shell, at a certain distance, a control panel 15 with additional openings 16 for the supply of treatment gas can be installed. The half shell is open at the top and the walls 4 or the floor are vertically adjustable so that the upper edge of the walls can be adjusted to be level with the neck of the patient. The treatment gas flows from the emanating devices located on the walls in the direction of the floor A which is purposely designed as a grate 4 - Fig.

We claim:

1. In a device for carrying out cryotherapy on the entire body of a patient with a cryogenic treatment gas consisting of a treatment chamber of insulating material for taking up the patient, which has connections for the supply and exhaust of the cryogenic treatment gas, the improvement being in that said treatment chamber is designed as a half shell, said half shell having a rear part and a side part on each side of said rear part with substantially its entire front being permanently open to permit a patient to freely walk into and out of said half shell and to permit an operator to readily monitor the treatment and to readily walk into said half shell during the treatment, said rear part having exhaust openings for the exhaust of the cryogenic treatment gas; and cryogenic treatment gas supply means, supply openings in said side parts of said half shell, said supply means feeding said cryogenic treatment to said supply openings, said supply openings being located laterally opposite said exhaust openings whereby the location of said supply and exhaust opening comprises means for flowing the treatment gas in a generally horizontal direction across said half shell.

2. Device according to claim 1 characterized therein that said half shell is formed by hollow profiles spanned by walls, said openings for the supply and exhaust of the treatment gas and said treatment gas supply means are installed in said hollow profiles, and said treatment gas supply means including openings in said hollow profiles.

3. Device according to claim 2, characterized therein that said openings for the supply and exhaust of the treatment gas are located in nozzle strips which are installed in said hollow profiles.

4. Device according to claim 2 wherein there are only three of said hollow profiles, and said exhaust openings being in the intermediate one of said profiles.

5. Device according to claim 3, characterized therein that said nozzle strips are adjustably mounted at different heights in said hollow profiles.

6. Device according to claim 5, characterized therein that said openings for the supply of the treatment gas are designed as tiltable nozzles in said nozzle strips.

7. Device according to claim 1, characterized by additional openings located in the vicinity of the floor for the removal of the treatment gas.

8. In a device for carrying out cryotherapy on the entire body of a patient with a cold treatment gas consisting of a treatment chamber of insulating material for taking up the patient, which has connections for the supply and exhaust of the treatment gas, the improvement being in that said treatment chamber is designed as a half shell, said half shell having a rear part and a side part on each side of said rear part with its front being open to permit a patient to freely walk into and out of said half shell and to permit an operator to readily monitor the treatment and to readily walk into said half shell during the treatment, said rear part having exhaust openings for the exhaust of the treatment gas; treatment gas supply means in said side parts of said half shell for flowing the treatment gas in a generally horizontal direction into said half shell, a control panel is mounted in front of said half shell at a predetermined distance which has aimed openings means for the supply of the treatment gas.

9. In a device for carrying out cryotherapy on the entire body of a patient with a cold treatment gas consisting of a treatment chamber of insulating material for taking up the patient, which has connections for the supply and exhaust of the treatment gas, the improvement being in that said treatment chamber is designed as a half shell, said half shell having a rear part and a side part on each side of said rear part with its front being open to permit a patient to freely walk into and out of said half shell and to permit an operator to readily monitor the treatment and to readily walk into said half shell during the treatment, said rear part having exhaust openings for the exhaust of the treatment gas; treatment gas supply means in said side parts of said half shell for flowing the treatment gas in a generally horizontal direction into said half shell, said half shell having open vertical edges at said side parts, a vertical nozzle strip having openings installed at each of said open vertical edges of said half shell, and said treatment gas supply means communicating with said nozzle strips.

10. Device according to claim 9, characterized therein that said nozzle strips are secured to said half shall by mounting means for being adjusted to selectively open predetermined openings for controlling the flow pattern of the treatment gas.

11. Device according to claim 9, characterized therein that said nozzle strips are secured to said half shell by mounting means for being rotated about their vertical axes.

12. Device according to claim 11 characterized by additional openings located in the vicinity of the floor for the removal of the treatment gas.

* * * * *